United States Patent
Shirai et al.

[11] Patent Number: 5,808,745
[45] Date of Patent: *Sep. 15, 1998

[54] METHOD FOR MEASURING A SUBSTITUTIONAL CARBON CONCENTRATION

[75] Inventors: Hiroshi Shirai, Kanagawa-ken; Mikio Watanabe, Sagae; Shinichiro Takasu, Tokyo, all of Japan

[73] Assignee: Toshiba Ceramics Co., Ltd., Tokyo, Japan

[ * ] Notice: The term of this patent shall not extend beyond the expiration date of Pat. No. 5,287,167.

[21] Appl. No.: 851,612

[22] Filed: May 6, 1997

Related U.S. Application Data

[63] Continuation of Ser. No. 704,234, Aug. 29, 1996, abandoned, which is a continuation of Ser. No. 490,833, Jun. 15, 1995, abandoned, which is a continuation of Ser. No. 217,021, Mar. 24, 1994, abandoned, which is a continuation of Ser. No. 751,193, Aug. 29, 1991, abandoned.

[30] Foreign Application Priority Data

Aug. 29, 1990 [JP] Japan .................................. 2-227453
Aug. 29, 1990 [JP] Japan .................................. 2-227454
Aug. 29, 1990 [JP] Japan .................................. 2-227455
Aug. 29, 1990 [JP] Japan .................................. 2-227456

[51] Int. Cl.$^6$ .......................... G01J 40/00; G01N 21/00
[52] U.S. Cl. ........................ 356/433; 356/364; 356/370; 356/351; 250/225
[58] Field of Search .................................. 356/364–370, 356/432–435, 345–346, 351, 448, 436; 250/360.1, 252.1, 341, 225

[56] References Cited

U.S. PATENT DOCUMENTS 4,590,574 5/1986 Edmonds et al. ........................ 356/346
5,007,741 4/1991 Carver et al. ............................ 356/448

FOREIGN PATENT DOCUMENTS 0 469 572 A3 2/1992 European Pat. Off. .

OTHER PUBLICATIONS

Stallhofer et al., "Oxygen and Carbon Measurements on Silicon Slices by the IR Method," Solid State Technology, vol. 26, No. 8, pp. 233–237 (Aug. 1983).

Shive et al., "Oxygen Determination in Silicon Using Fourier Transform Infrared Spectroscopy," Semiconductor Processing, ASTM STP 850, D.C. Gupta, Ed., Am. Soc. for Testing & Mat., 1984, pp. 320–324.

Baghdadi, "Multiple-Reflection Corrections in Fourier Transform Spectroscopy," Processing of the Symposium on Defects in Silicon, edited by W. Murray Bullis and L.C. Kimerling, pp. 293–302, The Electrochemical Society (1993).

(List continued on next page.)

*Primary Examiner*—Hoa Q. Pham
*Attorney, Agent, or Firm*—Foely & Lardner

[57] ABSTRACT

A silicon wafer measuring method includes: (a) a first step of measuring a light transmission characteristic ($I_{OBS}$) of the pulled silicon wafer by utilizing parallel polarized light incident at the Brewster angle into the pulled silicon wafer, (b) a second step of measuring a light transmission characteristic ($I_O$) of a floating zone silicon wafer functioning as a reference silicon wafer by utilizing parallel polarized light incident at the Brewster angle into the floating zone silicon wafer, and (c) a third step of calculating a substitutional carbon concentration [$C_{SC}$] on the basis of the light transmission characteristic ($I_{OBS}$) of the pulled silicon wafer measured during the first step and the light transmission characteristic ($I_O$) of the floating zone silicon wafer measured during the second step, (d) a fourth step of comparing the substitutional carbon concentration [$C_{SC}$] of the pulled silicon wafer measured during the third step with a reference value, and (e) a fifth step of removing a pulled silicon wafer if its substitutional carbon concentration [$C_{SC}$] outside of a range of values about the reference value so as to be defective in view of the results compared during the fourth step.

23 Claims, 5 Drawing Sheets

OTHER PUBLICATIONS

R.W. Series, "Determination of Oxygen and Carbon in Silicon Wafers," Royal Signals and Radar Establishment, Memorandum No. 3479, 1982.

H. Shirai, "Determination of Oxygen Concentration in Single Side Polished Czochralski–Grown Silicon Wafers by p–Polarized Brewster Angle Incidence Infrared Spectroscopy," J. Electrochemical Society, vol. 138, No. 6, pp. 1784–1787 (Jun. 1991).

H. Shirai, "Oxygen Measurements in Single Side Polished CZ–SI Wafers By p–Polarized Brewster Angle Incidence Infrared Spectroscopy," Extended Abstracts, 179th Electrochemical Society Meeting Washington, D.C., 1991, p. 704.

H. Shirai, "Oxygen Measurements on Commercial CZ–Si Wafers by p–Polarized Brewster–angle Incident FTIR," Extended Abstracts (The 5th Autumn Meeting, 1990), The Japan Society of Applied Physics, p. 287.

H. Shirai, "Study for the Measurements of Oxygen Concentration in Single–Side Polished CZ–Si Wafers by p–Polarized Brewster Angle Incidence Infrared Spectroscopy," Extended Abstracts (Autumn Meeting, 1990), The Spectroscopical Society of Japan, p. 54.

H. Shirai, "Oxygen Measurements on Wafers," Oyo Buturi, vol. 60, No. 8, p. 827 (1991).

"Measurement of Oxygen and Carbon Concentrations In Silicon Wafers By Using Infrared Vidicon Camera," IBM Technical Disclosure Bulletin, vol. 28, No. 3, Aug. 1985, pp. 1180–1181.

Bullis, "Measurement of Oxygen in Silicon," Solid State Technology, Mar. 1987, No. 3, pp. 69–72.

K. Krishnan—"Precise and Rapid Measurement of Oxygen and Carbon etc." Proceedings of the Symposium on Defects in Silicon, 1983, pp. 285–291.

K. Graff—"Precise Evaluation of Oxygen Measurements on CZ–Silicon Wafers"—J. Electrochem, Soc: Jun. 1983 pp. 1378–1381.

F. Schomann et al—"Correction Factors for the Determination of Oxygen etc." J. Electrochem, Soc. vol. 136, Jul. 1989 pp. 2025–2031.

J.A.A. Engelbrecht et al—"The Influence of Some Optical Parameters on IR Spectroscopy etc." Infrared Phys. vol. 26, No. 2, pp. 75–81.

J.A.A. Engelbrecht—"A Technique for Obtaining the Infrared Reflectivity of Back etc." J. Electrochem. Soc., vol. 137, No. 1, Jan. 1990, pp. 300–303.

Robert Graupner—"Analysis of Infrared Spectra for Oxygen Measurements etc." Silicon Processing, ASTM STP 804, 1983, pp. 459–468.

Leroueille—"Carbon Measurement in Thin Silicon Wafers etc." Applied Spectroscopy, vol. 36, No. 2, 1982, pp. 153–155.

"The Measurement of the Oxygen Concentration of Silicon Wafers by Fourier–transform–Infrared–Spectroscopy" Materialpreufung, vol. 32, p. 110 (1990).

METHOD FOR MEASURING A SUBSTITUTIONAL CARBON CONCENTRATION

This application is a continuation of application Ser. No. 08/704,234, filed on Aug. 29, 1996, now abandoned which is a continuation of application Ser. No. 08/490,833, filed Jun. 15, 1995, now abandoned, which is a continuation of application Ser. No. 08/217,021, filed Mar. 24, 1994, now abandoned, which is a continuation of application Ser. No. 07/751,193, filed Aug. 29, 1991, now abandoned.

BACKGROUND OF THE INVENTION

1. Field of the Invention

The present invention relates to a method for making a silicon wafer. In particular, the present invention relates to a method for making a silicon wafer in which the substitutional carbon concentration of a pulled silicon wafer is calculated on the basis of a light transmission characteristic measured by utilizing parallel polarized light incident at the Brewster angle into the pulled silicon wafer and a further light transmission characteristic measured by incidence of parallel polarized light at the Brewster angle into a floating zone silicon wafer functioning as a reference silicon wafer.

2. Description of Related Art

In the conventional method for making silicon wafers, a pulled silicon wafer is picked up from a production line in order to inspect it. A floating zone type silicon wafer is utilized as a reference wafer since the carbon concentration of such wafers is known to be negligibly small. The reference silicon wafer is prepared so as to have substantially the same optical behavior as that of the pulled silicon wafer, for example, by mirror polishing and chemically polishing of the front and rear sides thereof, depending on a treated condition of the pulled silicon wafer when it is picked up. In particular, the reference silicon wafer must be treated so as to correspond to the picked-up silicon wafer. After that, infrared radiation impinges on the pulled silicon wafer and the reference silicon wafer at the same time to thereby measure a light transmission characteristic of the pulled silicon wafer and the floating zone silicon wafer so that the substitutional carbon concentration of the pulled silicon wafer is calculated. The pulled silicon wafer is determined to be defective or not depending upon the calculated substitutional carbon concentration values.

Such a conventional silicon wafer production method has the disadvantage that the pulled silicon wafer and the floating zone silicon wafer must have substantially the same optical behavior e.g., they must both be mirror polished. Further disadvantages are:

(i) A lot of time and complicated measuring operations are required.

(ii) It is not possible in practice to inspect all of pulled silicon wafers on a production line.

(iii) Since machining takes place prior to the measurement, defective wafers are unnecessary machined thereby reducing efficiency.

(iv) As a result, it is difficult to improve the production efficiency of the production line.

SUMMARY OF THE INVENTION

It is an object of the present invention to provide a method for making a silicon wafer in which a floating zone silicon wafer having both front and rear mirror polished surfaces can be used as a reference silicon wafer without any additional treatment.

It is another object of the present invention to provide a method for measuring a substitutional carbon concentration of a silicon wafer in which the measuring operation is simple.

It is a further object of the present invention to provide a method for measuring a substitutional carbon concentration of a silicon wafer in which all of pulled silicon wafers on a production line can be detected with respect to substitutional carbon concentration.

According to the present invention, a silicon wafer measuring method includes:

(a) a first step of measuring a light transmission characteristic ($I_{OBS}$) of the pulled silicon wafer by utilizing parallel polarized light incident at the Brewster angle on the pulled silicon wafer, (b) a second step of measuring a light transmission characteristic ($I_O$) of a floating zone silicon wafer functioning as a reference silicon wafer, both front and rear surfaces of which are mirror polished, by utilizing parallel polarized light incident at the Brewster angle on the floating zone silicon wafer, and (c) a third step of calculating a substitutional carbon concentration [$C_{SC}$] on the basis of the light transmission characteristic ($I_{OBS}$) of the pulled silicon wafer measured during the first step and the light transmission characteristic ($I_O$) of the floating zone silicon wafer measured during the second step.

According to the present invention, also, a silicon wafer production method in which a pulled silicon wafer cut from a pulled silicon single crystal is subject to a series of treatments, includes:

(a) a first step of measuring a light transmission characteristic ($I_{OBS}$) of the pulled silicon wafer by utilizing parallel polarized light incident at the Brewster angle into the pulled silicon wafer, (b) a second step of measuring a light transmission characteristic ($I_O$) of a floating zone silicon wafer functioning as a reference silicon wafer, both front and rear surfaces of which are mirror polished, by utilizing parallel polarized light incident at the Brewster angle into the floating zone silicon wafer, and (c) a third step of calculating a substitutional carbon concentration [$C_{SC}$] on the basis of the light transmission characteristic ($I_{OBS}$) of the pulled silicon wafer measured during the first step and the light transmission characteristic ($I_O$) of the floating zone silicon wafer measured during the second step.

The series of treatments may be preformed on the pulled silicon wafer includes chemically polishing (etching), mirror polishing, detecting, removing, washing, and gettering.

It is preferable that the method of the present invention includes further:

(d) a fourth step of comparing the substitutional carbon concentration [$C_{SC}$] of the pulled silicon wafer measured during the third step with a reference value, and (e) a fifth step of removing a pulled silicon wafer if its substitutional carbon concentration [$C_{SC}$] is outside a range of values about the reference value so as to determine a defective wafer in view of the results compared during the fourth step.

During the first step, the light transmission characteristic of the pulled silicon wafer can be measured in various ways. One example is to utilize a pulled silicon wafer which has a mirror polished front surface and a non-polished rear surface. In another example, both front and rear surfaces are chemically polished but not mirror polished.

The term "parallel polarized light" means polarized light which is substantially linearly polarized in a direction parallel to the incident plane (the plane defined by the direction of the incident light and the normal to the wafer surface). The wafer surface may be, for example, a polished wafer and a non-polished wafer. Examples of the polished wafer may include a single-side polished wafer and a double-side polished wafer and also a chemically and/or mirror polished pulled silicon wafer and a mirror polished floating zone silicon wafer which has both front and rear surfaces mirror polished. Also, the term "pulled silicon wafer" means a silicon wafer which is cut from a pulled silicon single crystal produced by a pulling method or so called Czochralski method and then treated, if desired, in various manners. Such a silicon wafer is usually made by a series of steps of cutting (slicing), mechanical polishing (lapping), chemical polishing (etching) and mirror polishing in order together with intermediate washing and optional gettering steps although the present invention is not limited to such precise steps. The chemical polishing step is usually performed after the mechanical polishing step. The chemical polishing step is used to remove damaged layers in the front and rear surfaces of the silicon wafer which is formed during the step of cutting a single crystal. In addition, the term "floating zone silicon wafer" means a silicon wafer which is cut from a silicon single crystal made by the well known floating zone melting method.

The present invention can have the following advantageous effects:

(i) A floating zone silicon wafer, both front and rear surfaces of which are mirror polished, can be used as it is without any additional treatment;

(ii) the operation of measuring substitutional carbon concentration $[C_{SC}]$ of a pulled silicon wafer can be simple;

(iii) the step of measuring substitutional carbon concentration $[C_{SC}]$ of a pulled silicon wafer can be carried out at a desired position in a production line in order to detect all wafers; and (iv) the production coefficient on the production line can be improved.

BRIEF DESCRIPTION OF THE DRAWINGS

The invention is described in reference to the following detailed description taken in conjunction with the drawings in which.

DETAILED DESCRIPTION OF THE PREFERRED EMBODIMENTS

Embodiment 1

Figure 1:
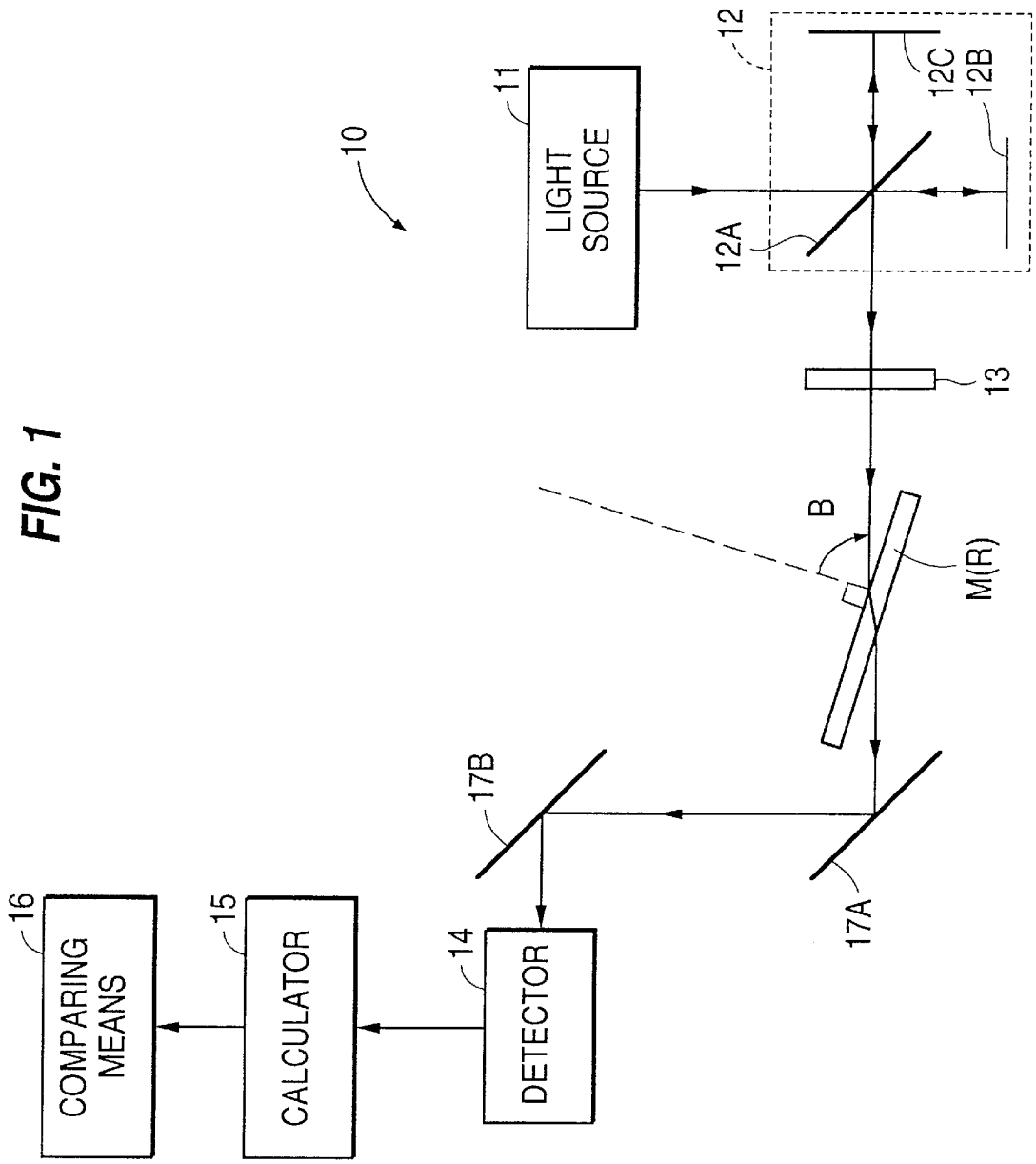
FIG. 1 is a schematic view showing an apparatus for carrying out a preferred silicon wafer measuring method according to an embodiment of the present invention.

A first embodiment of the present invention will be described, referring to FIG. 1.

According to the first embodiment of the present invention, a method for making a silicon wafer includes the step of measuring substitutional carbon concentration prior to the steps of gettering and mirror polishing after the washing step accompanied by the chemically polishing step for silicon wafers on a production line.

The measuring step in the silicon wafer production method according to the present invention includes a first step of measuring a light transmission characteristic (herein called transmitted light intensity $I_{OBS}$) of a pulled silicon wafer by using parallel polarized light incident at the Brewster angle B into the pulled silicon wafer. Both the front and rear surfaces of the wafer are previously chemically polished during a chemically polishing step within the production line and then washed during a washing step. A second step of the method involves measuring a light transmission characteristic (herein called transmitted light intensity $I_O$) of a floating zone silicon wafer functioning as a reference silicon wafer, having mirror polished front and rear sides, by directing of parallel polarized light incident at the Brewster angle B into the reference or floating zone silicon wafer. A third step involves calculating a substitutional carbon concentration $[C_{SC}]$ on the basis of the light transmission characteristic or transmitted light intensity $I_{OBS}$ of the chemically polished pulled silicon wafer measured during the first step and the light transmission characteristic or transmitted light intensity $I_O$ of the mirror polished floating zone silicon wafer or reference silicon wafer measured during the second step. A fourth step involves comparing the substitutional carbon concentration $[C_{SC}]$ of the pulled silicon wafer calculated during the third step with a reference value, and a fifth step involves removing a pulled silicon wafer if its substitutional carbon concentration $[C_{SC}]$ is not within an acceptable range adjacent the reference value so as to be defective in view of the comparison results in the fourth step.

During the first and second steps, the parallel polarized light enters into both the chemically polished pulled silicon wafer and the mirror polished floating zone silicon wafer at the Brewster angle B. This arrangement is used because any substantial reflection is avoided at the Brewster angle when the parallel polarized light moves in and though the chemically polished pulled silicon wafer and the mirror polished floating zone silicon wafer whereby multiple reflections can be avoided within the chemically polished pulled silicon wafer and the mirror polished floating zone silicon wafer.

During the second step, the floating zone silicon wafer is used as a reference silicon wafer because the substitutional carbon concentration $[C_{SC}]$ of the floating zone silicon wafer is much smaller than that of the pulled silicon wafer and may be considered negligible.

Also, both front and rear surfaces of the floating zone silicon wafer are mirror polished because the incidence light or parallel polarized light is intended to be prevented from being scattered at both front and rear surfaces thereof.

During the third step, the substitutional carbon concentration of the pulled silicon wafer is calculated on the basis of the light transmission characteristic or transmitted light intensity $I_{OBS}$ of the chemically polished pulled silicon wafer measured during the first step and the light transmission characteristic or transmitted light intensity $I_O$ of the floating zone silicon wafer measured during the second step. This calculation step is explained below.

First, by using the light absorption coefficient E resulting from the vibration of the substitutional carbon in the pulled silicon wafer and the conversion coefficient k which may be taken to be $1.1 \times 10^{17}$ number/$cm^2$, the substitutional carbon concentration $C_{SC}$ of the pulled silicon wafer can be expressed by the following formula:

$$[C_{SC}] = k \times E$$

By using the light absorbance A of the silicon wafer having a thickness d with the wave number of 607 cm$^{-1}$ resulting from the vibration of the substitutional carbon and the optical path (L=1.042d) of the parallel polarized light which enters at the Brewster angle B, the light absorption coefficient E of the pulled silicon wafer can be expressed according to Lambert-Beer's law as follows:

$$E = A/L = A/1.042d$$

By using the light transmission characteristic or transmitted light intensity (in the general case designated I) of the pulled silicon wafer of which both front and rear surfaces are mirror polished and the light transmission characteristic or transmitted light intensity $I_O$ of the floating zone silicon wafer which is mirror polished, the light absorbance A of the pulled silicon wafer can be expressed as follows:

$$A = \ln (I/I_O)^{-1}$$

Thus, by using the light transmission characteristic or transmitted light intensity $I_{OBS}$ of the chemically polished pulled silicon wafer, the light transmission characteristic or transmitted light intensity $I_O$ of the mirror polished floating zone silicon wafer, the light scattering characteristic or scattered light intensity $I_{S1}$ of the chemically polished pulled silicon wafer at its front surface, and the light scattering characteristic or scattered light intensity $I_{S2}$ of the chemically polished pulled silicon wafer at its rear surface, the light absorbance A can be also expressed as follows:

$$A = \ln [(I_{OBS} + I_{S1} + I_{S2})/I_O]^{-1}$$

Accordingly, the substitutional carbon concentration [$C_{SC}$] of the pulled silicon wafer can be calculated as follows:

$$[C_{SC}] = (k/1.042d) \times \ln [(I_{OBS} + I_{S1} + I_{S2})/I_O]^{-1}$$

The value of $\ln [(I_{OBS} + I_{S1} + I_{S2})/I_O]^{-1}$ can be obtained from light absorbance characteristic which is the natural logarithm of an inverse of the ratio of the total of the light transmission characteristic or transmitted light intensity $I_{OBS}$ of the chemically polished pulled silicon wafer, the light scattering characteristic or scattered light intensity $I_{S1}$ at the front side of the chemically polished pulled silicon wafer and the light scattering characteristic or scattered light intensity $I_{S2}$ at the rear surface of the chemically polished pulled silicon wafer to the light transmission characteristic or transmitted light intensity $I_O$ of the mirror polished floating zone silicon wafer.

Figure 3:
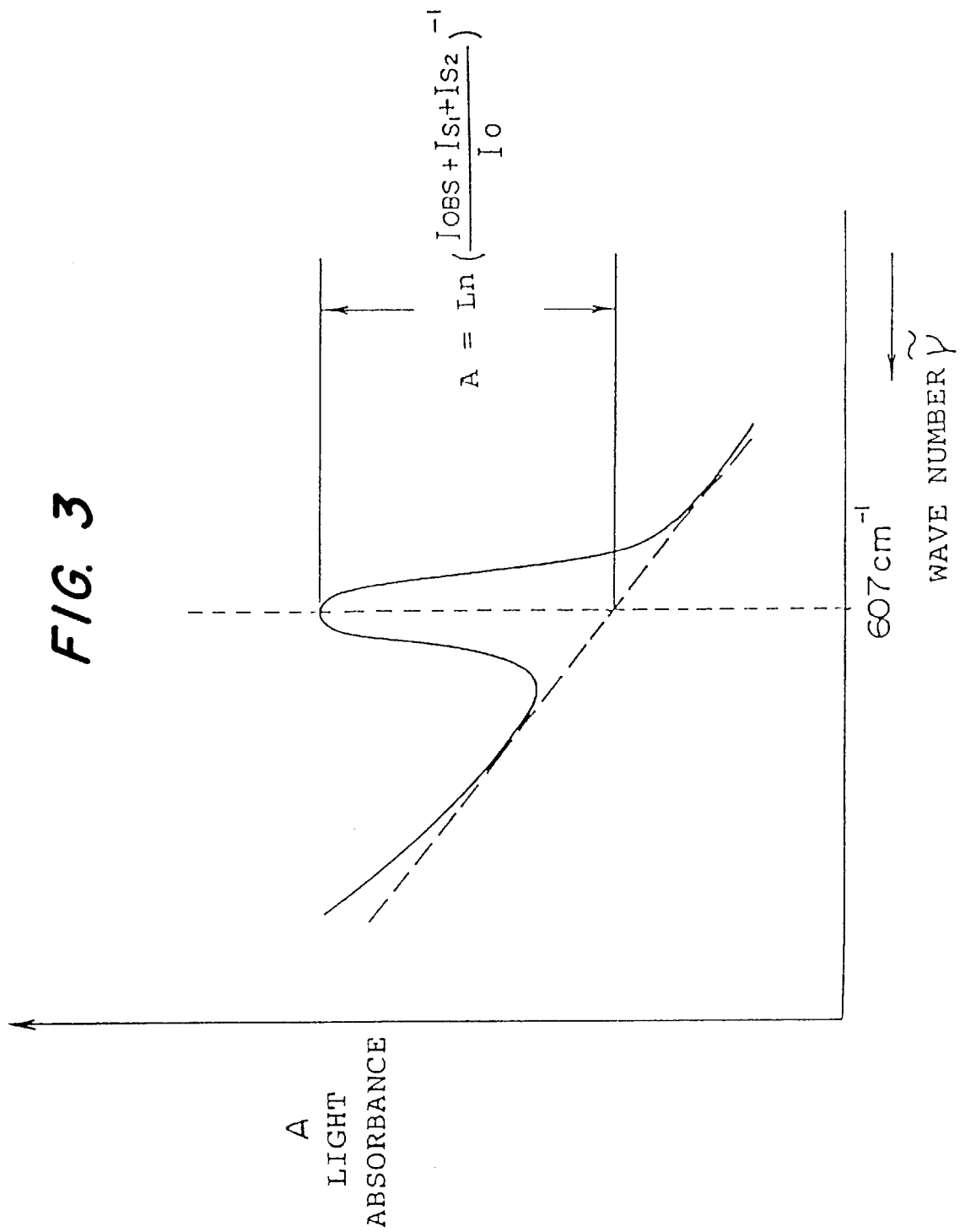
FIG. 3 is a graph explaining the measurement principle in accordance with the present invention.

For example, the value of $\ln [(I_{OBS} + I_{S1} + I_{S2})/I_O]^{-1}$ can be obtained as shown in FIG. 3, by using the difference between the peak value of the light absorption characteristic designated by the solid line characteristic of the substitutional carbon absorption line of wave number 607 cm$^{-1}$ when the substitutional carbon concentration [$C_{SC}$] is not zero, i.e., the pulled silicon wafer, and the value of the light absorption characteristic designated by the inclined dotted line when the substitutional carbon concentration [$C_{SC}$] is zero, i.e., the floating zone silicon wafer.

An apparatus for carrying out the first embodiment of the present invention is explained below.

Figure 2:
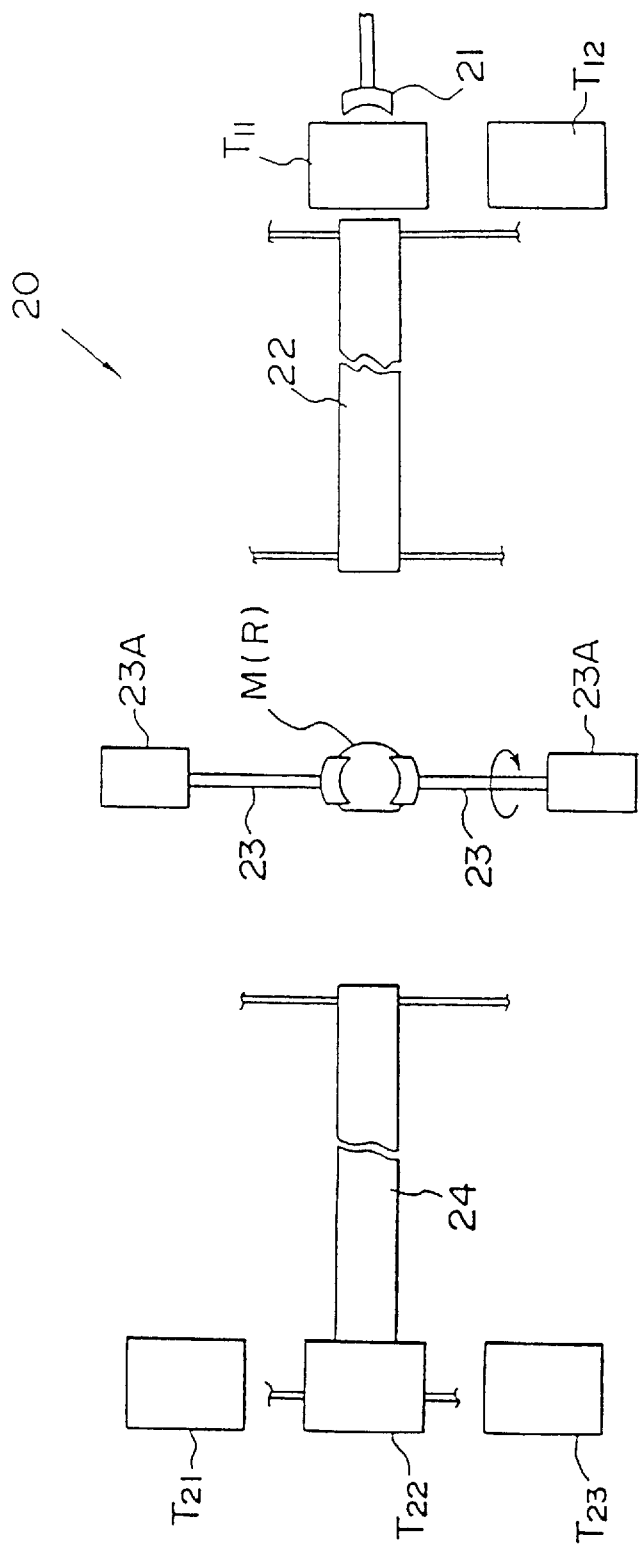
FIG. 2 is a schematic view showing a transfer means for use in the embodiment of the present invention.

Referring to FIGS. 1 and 2, a measuring apparatus 10 for carrying out the first embodiment includes a light source 11 such as a globe lamp and a Michelson interferometer 12 for forming interference light beams. The interferometer 12 uses a semi-transparent mirror or half mirror 12A functioning as a beam splitter, a movable mirror 12B and a fixed mirror 12C. The apparatus further comprises a polarizer 13 for providing a sample or chemically polished pulled silicon wafer M and a reference silicon wafer or mirror polished floating zone silicon wafer R with parallel polarized light which is polarized from the interference light given by the Michelson interferometer 12. The sample M is transferred into the measurement position by a transfer means 20 shown in FIG. 2. The apparatus further includes a detector 14 for detecting the light transmission characteristic (or transmitted light intensity $I_{OBS}$ of the parallel polarized light) of the sample M and the light transmission characteristic (or transmitted light intensity $I_O$ of the parallel polarized light) of the reference R, a calculator 15 connected to the detector 14 for calculating the substitutional carbon concentration of the sample M after the light absorbance characteristic is calculated on the basis of the light transmission characteristic or transmitted light intensity $I_{OBS}$ of the sample M and the light transmission characteristic or transmitted light intensity $I_O$ of the reference R, and a means for comparing a reference value with a value of the substitutional carbon concentration which is calculated by the calculator 15.

If desired, reflecting mirrors 17A, 17B are provided between the sample M and the detector 14 and/or between the reference R and the detector 14. Also, a reflecting mirror (not shown) can be arranged between the Michelson interferometer 12 and the polarizer 13.

The transfer means 20 includes a pushing member 21 for pushing the sample M and the reference R from a plurality of transfer containers $T_{11}$, $T_{12}$ one by one, a transfer belt 22 for transferring the sample M and the reference R pushed by the pushing means 21 one by one from one end thereof to the other end thereof, a holding means 23 for holding the sample M and the reference R one by one at the other end of the transfer belt 22 and then transferring the same to a measuring area where the sample M and the reference R are rotated by a rotation means 23A until they are oriented at the Brewster angle B with respect to the parallel polarized light. After the substitutional carbon concentration thereof is measured, the sample M and the reference R are again rotated by the rotation means 23A so as to come back to their original position and then move out of the measuring area. The transfer means 20 further includes another transfer belt 24 for receiving the sample M and the reference R which are released from the measuring area by means of the holding means 23 and then transferring them from one end of the transfer belt 24 to the other end thereof where a plurality of transfer containers $T_{21}$, $T_{22}$ are placed.

Although in the illustrated embodiment the reference R is contained in the transfer container $T_{12}$, the reference R and the sample M together can be contained in the transfer container $T_{11}$. In this case, the transfer container $T_{12}$ can be omitted.

For example, the transfer containers $T_{21}$, $T_{22}$, $T_{23}$ are used, respectively, for containing defective sample M which has a value of substitutional carbon concentration more than the reference value, a transfer container for containing proper sample M which has a value of substitutional carbon concentration less than the reference value, and a transfer container for containing the reference R.

The transfer containers $T_{21}$, $T_{22}$, $T_{23}$ are designed to receive the samples M in response to the comparison results of the comparison means 16 in the measuring apparatus 10. The transfer containers move to an end of the transfer belt 24 so as to receive the reference R.

In the measuring apparatus 10, the Michelson interferometer 12 receives the light from the light source 11 and then produces interference light. This interference light is further filtered so as to obtain parallel polarized light by means of the polarizer 13. After that, the parallel polarized light is incident at the Brewster angle B into the sample M and the reference R which are transferred to the measuring area by the transfer means 20.

The light is absorbed and scattered in the sample M and the reference R according to the optical properties thereof. Therefore, the light absorbance characteristic, which can be calculated by the calculator 15 on the basis of the signals detected by the detector 14, is shown in FIG. 3 by way of example.

According to FIG. 3 or a table corresponding to it, the calculator 15 calculates the following formula:

$$\ln \left[(I_{OBS}+I_{S1}+I_{S2})/I_O\right]^{-1}$$

After that, the calculator 15 calculates the light absorbance coefficient E of the chemically polished, pulled silicon wafer by the following formula:

$$E=(1/1.042d)\times \ln \left[(I_{OBS}+I_{S1}+I_{S2})/I_O\right]^{-1}$$

In addition, the calculator calculates the substitutional carbon concentration $[C_S]$ of the sample M of the chemically polished pulled silicon wafer M by the following formula:

$$[C_{SC}]=(k/1.042d)\times \ln \left[(I_{OBS}+I_{S1}+I_{S2})/I_O\right]^{-1}$$

After that, the comparison means 16 compares the reference value with the value of the substitutional carbon concentration $[C_{SC}]$ of the sample or chemically polished, pulled silicon wafer M which is calculated by the calculator 15.

The results of the comparison means 16 are sent to means for controlling the transfer means 20 to be used in transferring the sample M and the reference R into the transfer containers $T_{21}$, $T_{22}$, $T_{23}$.

EXAMPLES 1 TO 7

Working examples of the first embodiment will be explained so that a method for making a silicon wafer according to the present invention will be fully understood.

As shown in Table 1, substitutional carbon concentration $[C_{SC}]$ of plural pulled silicon wafers were measured according to the present invention. Each silicon wafer were chemically polished on both front and rear surfaces.

After that, both front and rear sides of those pulled silicon wafers were mirror polished. In such a mirror polished condition, the substitutional carbon concentration $[C_{SC}]^*$ of each pulled silicon wafer was measured according to the present invention.

Figure 4:
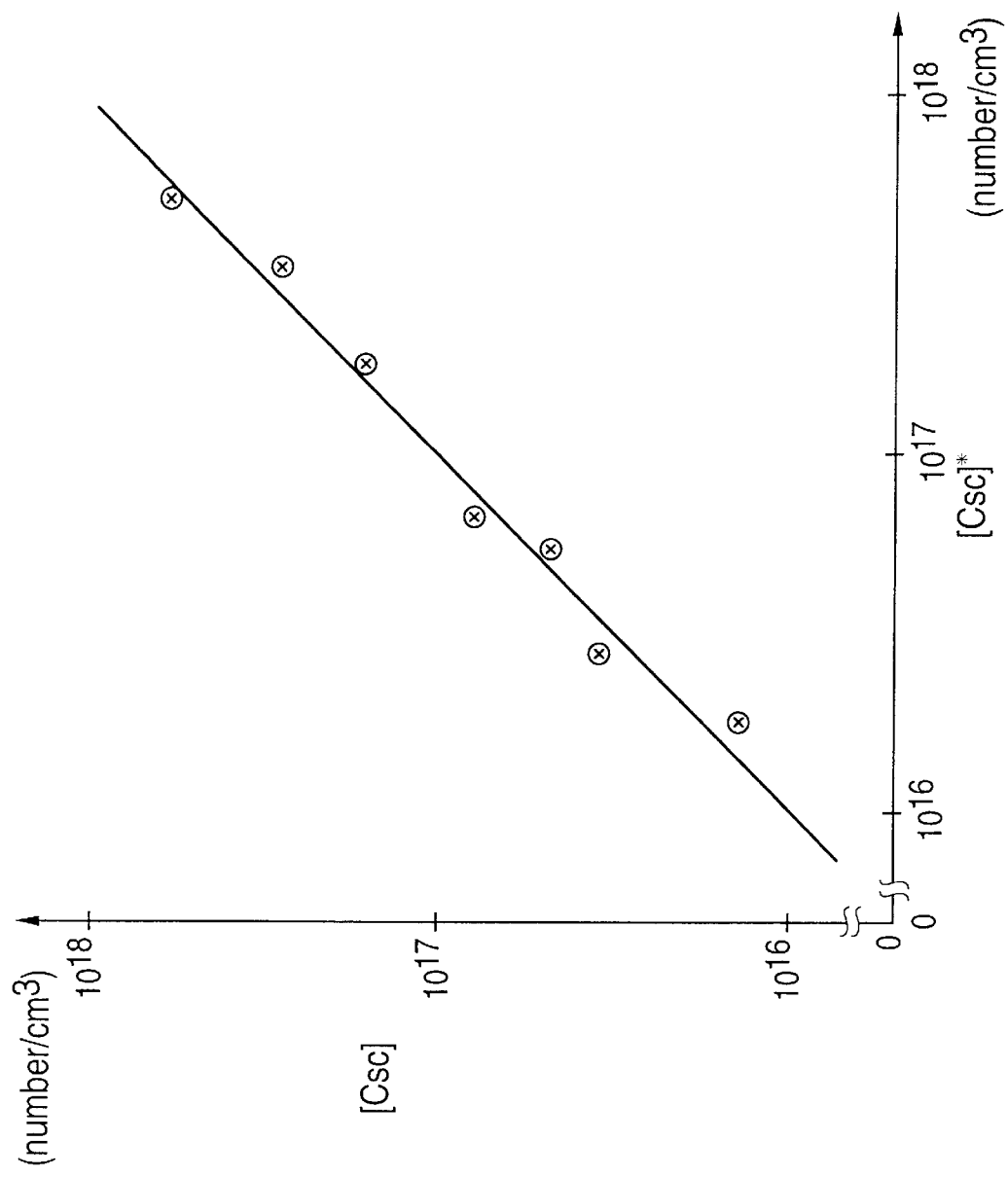
FIG. 4 is a graph explaining and showing the results of working examples in accordance with another embodiment of the present invention.

Such measured results of the substitutional carbon concentration $[C_{SC}]$ of the chemically polished pulled silicon wafers and the substitutional carbon concentration $[C_{SC}]^*$ of the subsequently produced two-side mirror polished pulled silicon wafers are plotted along the Y-axis and X-axis, respectively, in FIG. 4. This graph shows that the former reasonably corresponds to the latter so that the test results are positioned along the line X=Y.

It is apparent from the examples 1 to 7 that, according to the present invention, the chemically polished pulled silicon wafers and the mirror polished floating zone silicon wafers can be used as sample and references, respectively, in order to directly measure substitutional carbon concentration $[C_{SC}]$ of the pulled silicon wafers on the production line. Thus it is not necessary to make the measurement on the two-side mirror polished pulled silicon wafer, even though a floating zone silicon wafer is used have both front and rear surfaces mirror polished.

TABLE 1

| Example No. | substitutional carbon concentration $[C_{sc}]$ of chemically polished pulled silicon wafer ($\times 10^{16}$ number/cm$^3$) | substitutional carbon concentration $[C_{sc}]^*$ of mirror polished pulled silicon wafer ($\times 10^{16}$ number/cm$^3$) |
|---|---|---|
| 1 | 1.4 | 1.8 |
| 2 | 3.5 | 2.8 |
| 3 | 4.7 | 5.4 |
| 4 | 7.8 | 6.6 |
| 5 | 16 | 18 |
| 6 | 28 | 34 |
| 7 | 58 | 52 |

The present invention is not limited to the embodiments in which the Michelson interferometer 12 is used. For example, a spectrometer can be used in place of the Michelson interferometer.

In general, the production of the pulled silicon wafer involves growing the silicon crystal, cutting the crystal, washing and lapping the surface of both surfaces to provide a coarse polishing (mechanically polishing), washing and chemically polishing the surface and then washing and mirror polishing the surface. A gettering step may be used at various points in the process such as before and/or after the mirror polishing step.

Although in the above-stated embodiments the substitutional carbon concentration $[C_{SC}]$ is measured prior to the gettering step following the chemically polishing step, the present invention is not restricted to such embodiment. For example, the substitutional carbon concentration $[C_{SC}]$ can be measured at any position or place after the chemically polishing step and prior to the mirror polishing step.

Embodiment 2

A second embodiment of the present invention will be explained with respect to the construction and operation thereof.

The second embodiment of the present invention has substantially the same construction as that of the first embodiment except that, in addition to the substitutional carbon concentration measuring step prior to the gettering step, the substitutional carbon concentration measuring step is carried out after the gettering step.

The substitutional carbon concentration measuring step after the gettering step has the same construction as that of the substitutional carbon concentration measuring step prior to the gettering step which corresponds to the measuring step in the first embodiment.

The operation of the second embodiment can be easily understood by taking into consideration that of the first embodiment. Thus, the explanation thereof is omitted.

Embodiment 3

A third embodiment of the present invention will be explained with respect to the construction and operation thereof.

The third embodiment of the present invention has substantially the same construction as that of the first embodiment except that, in place of the substitutional carbon concentration measuring step prior to the gettering step, the substitutional carbon concentration measuring step is carried out after the gettering step.

The substitutional carbon concentration measuring step after the gettering step has the same construction as that of the measuring step in the first embodiment.

The operation of the third embodiment can be easily understood by taking into consideration that of the first embodiment. Thus, the explanation thereof is omitted.

Embodiments 4, 5 and 6

Embodiments 4, 5 and 6 of the present invention have substantially the same construction as that of the embodiments 1, 2 and 3, respectively, except that the fourth comparing step and the fifth removing step of the embodiments 1, 2 and 3 are omitted.

The operation of the embodiments 4, 5 and 6 can be easily understood by taking into consideration that of the embodiments 1, 2 and 3, respectively.

Embodiment 7

A seventh embodiment of the present invention is similar to the first embodiment except that the sample has a mirror polished front surface and non-mirror polished rear surface. In order to easily ascertain front and rear surfaces of the silicon wafer during subsequent treatments thereof, only the front surface is mirror polished while the rear surface is not mirror polished.

The measuring step includes a first step of measuring a light transmission characteristic or transmitted light intensity $I_{OBS}$ of a pulled silicon wafer (herein called one-side polished silicon wafer) by directing of parallel polarized light at the Brewster angle B into the pulled silicon wafer. Only a front surface of the wafer is mirror polished during the mirror polishing step within the production line and then washed during a washing step. A second step consists of measuring a light transmission characteristic or transmitted light intensity $I_O$ of a floating zone silicon wafer functioning as a reference silicon wafer by using parallel polarized light at the Brewster angle B directed into the reference silicon wafer or floating zone silicon wafer. Both front and rear surfaces of the reference wafer are mirror polished. A third step consists of calculating a substitutional carbon concentration $[C_{SC}]$ on the basis of the light transmission characteristic or transmitted light intensity $I_{OBS}$ of the one-face polished pulled silicon wafer measured during the first step and the light transmission characteristic or transmitted light intensity $I_O$ of the mirror polished floating zone silicon wafer or reference silicon wafer measured during the second step. A fourth step consists of comparing the substitutional carbon concentration $[C_{SC}]$ of the pulled silicon wafer measured during the third step with a reference value, and a fifth step of removing a defective pulled silicon wafer if its substitutional carbon concentration $[C_{SC}]$ is not within a range of values about the reference value (for example, between the an upper limit reference value and a lower limit reference value). In this embodiment, as well as in the other embodiments described herein, the reference value and the acceptable range about the reference value (defined by upper and lower limit reference values) is selected depending upon customer requirements and/or the particular application for the pulled silicon wafer, e.g., power transistor, diode, IC chip, etc.

During the first and second steps, the parallel polarized light enters into both the one-face polished pulled silicon wafer and the mirror polished floating zone silicon wafer at the Brewster angle B because any substantial reflection is avoided when the parallel polarized light moves in and through the one-side polished pulled silicon wafer and the mirror polished floating zone silicon wafer whereby multiple reflections can be avoided within the one-face polished pulled silicon wafer and the mirror polished floating zone silicon wafer.

During the third step, the substitutional carbon concentration of the one-side polished pulled silicon wafer is calculated on the basis of the light transmission characteristic or transmitted light intensity $I_{OBS}$ of the one-side polished pulled silicon wafer measured during the first step and the light transmission characteristic or transmitted light intensity $I_O$ of the mirror polished floating zone silicon wafer measured during the second step. This calculation is substantially the same as that of the first embodiment except that the light absorbance A is expressed as follows:

$$A = ln\,[(I_{OBS}+I_S)/I_O]^{-1}$$

Only the light scattering characteristic or scattered light intensity $I_S$ of the one-side polished pulled silicon wafer at its rear surface is used and the light scattering characteristic or scattered light intensity of the one-side polished pulled silicon wafer at its front surface is disregarded because the front side of the pulled silicon wafer is mirror polished.

EXAMPLES 8 TO 13

Working examples of the seventh embodiment will be explained so that a method for making a silicon wafer according to the present invention will be fully understood.

As shown in Table 2, substitutional carbon concentration $[C_{SC}]$ of plural pulled silicon wafers were measured according to the present invention. First, a silicon wafer, only a front surface of which was mirror polished, that is, one-side polished silicon wafer was measured with respect to its substitutional carbon concentration $[C_{SC}]$.

After that, the pulled silicon wafer was mirror polished on the rear sides thereof to produce a two-side polished sample, and the substitutional carbon concentration $[C_{SC}]^*$ of each two-side polished silicon wafer was measured according to the present invention.

Figure 5:
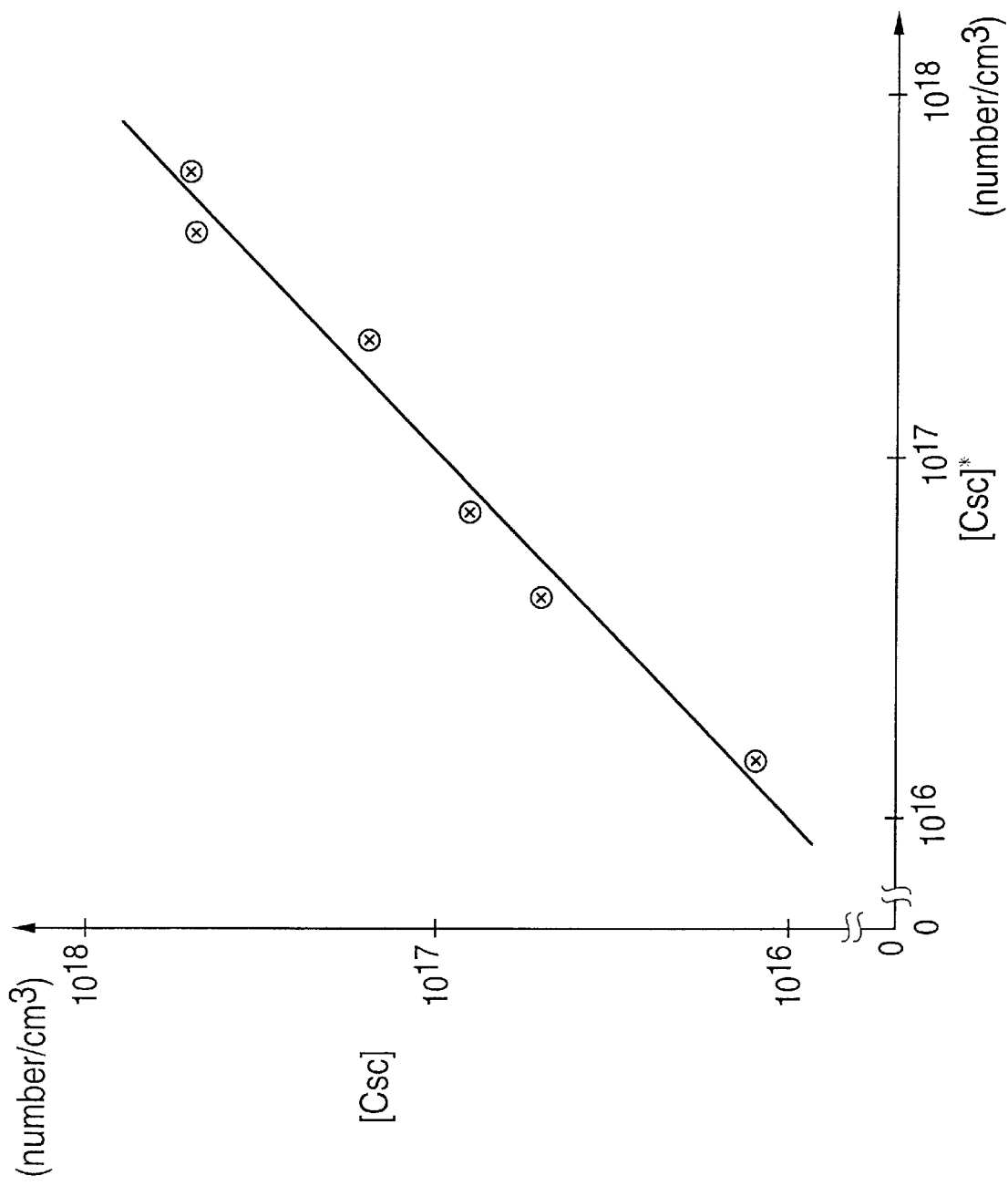
FIG. 5 is a graph showing another embodiment of the present invention.

Such measured results of the substitutional carbon concentration $[C_{SC}]$ of the one-side polished pulled silicon wafers and the substitutional carbon concentration $[C_{SC}]^*$ of the two-side mirror polished pulled silicon wafers are plotted along the Y-axis and X-axis, respectively, in FIG. 5. Thus, the former reasonably corresponds to the latter so that the test results are positioned along the line X=Y.

It is apparent from the examples 8 to 13 that, according to the present invention, the one-side polished pulled silicon wafers and the mirror polished floating zone silicon wafers can be used as sample and references, respectively, in order to directly measure substitutional carbon concentration $[C_{SC}]$ of the two-side polished pulled silicon wafers on the production line.

The present invention is not limited to the embodiment in which the Michelson interferometer 12 is used.

Although in the above-stated embodiments the substitutional carbon concentration $[C_{SC}]$ is measured prior to the gettering step following the mirror polishing step, the present invention is not restricted to such embodiments only. For example, the substitutional carbon concentration $[C_{SC}]$ can be measured at any position or place after the chemically polishing step. For instance, the substitutional carbon concentration $[C_{SC}]$ can be measured during a silicon wafer detecting step just before the silicon wafers are shipped.

TABLE 2

| Example No. | substitutional carbon concentration [$C_{sc}$] of one-side polished pulled silicon wafer ($\times 10^{16}$ number/cm$^3$) | substitutional carbon concentration [$C_{sc}$]* of two-side polished pulled silicon wafer ($\times 10^{16}$ number/cm$^3$) |
|---|---|---|
| 8 | 1.3 | 1.5 |
| 9 | 5.2 | 4.3 |
| 10 | 8.6 | 7.3 |
| 11 | 17 | 22 |
| 12 | 54 | 42 |
| 13 | 56 | 62 |

Embodiment 8

An eighth embodiment of the present invention will be explained with respect to the construction and operation thereof.

The eighth embodiment of the present invention has substantially the same construction as that of the seventh embodiment except that, in addition to the substitutional carbon concentration measuring step prior to the gettering step, a substitutional carbon concentration measuring step is carried out after the gettering step.

The substitutional carbon concentration measuring step subsequent to the gettering step has the same construction as that of the substitutional carbon concentration measuring step prior to the gettering step which corresponds to the measuring step in the seventh embodiment.

The operation of the eighth embodiment can be easily understood by taking into consideration that of the seventh embodiment. Thus, the explanation thereof is omitted.

Embodiment 9

A ninth embodiment of the present invention will be explained with respect to the construction and operation thereof.

The ninth embodiment of the present invention has substantially the same construction as that of the seventh embodiment except that, in place of the substitutional carbon concentration measuring step prior to the gettering step, the substitutional carbon concentration measuring step is carried out after the gettering step.

The substitutional carbon concentration measuring step after the gettering step has the same construction as that of the measuring step in the seventh embodiment.

The operation of the ninth embodiment can be easily understood by taking into consideration that of the seventh embodiment. Thus, the explanation thereof is omitted.

Embodiments 10, 11 and 12

Embodiments 10, 11 and 12 of the present invention have substantially the same construction as that of the embodiments 7, 8 and 9, respectively, except that the fourth comparing step and the fifth removing step of the embodiments 7, 8 and 9 are omitted.

The operation of the embodiments 10, 11 and 12 can be easily understood by taking into consideration that of the embodiments 7, 8 and 9, respectively.

The measured results of the substitutional carbon concentration [$C_{SC}$] of the one-side mirror polished pulled silicon wafers and the substitutional carbon concentration [$C_{SC}$]* of the two-side mirror polished pulled silicon wafers are plotted along the Y-axis and X-axis, respectively, in FIG. 5. Thus, the former reasonably corresponds to the latter so that the test results are positioned along the line X=Y.

What is claimed is:

1. A method for measuring a substitutional carbon concentration of a pulled silicon wafer, said measuring method comprising the steps of:

(a) a first step of measuring a light transmission characteristic ($I_{OBS}$) of the pulled silicon wafer by utilizing parallel polarized light incident at a Brewster angle into the pulled silicon wafer, wherein the Brewster angle is an angle defined between the parallel polarized light and a line which is perpendicular to a face of the pulled silicon wafer;

(b) a second step of measuring a light transmission characteristic ($I_O$) of a floating zone silicon wafer functioning as a reference silicon wafer both front and rear faces of which are mirror polished, by utilizing parallel polarized light incident at the Brewster angle into the floating zone silicon wafer; and (c) a third step of directly calculating a substitutional carbon concentration throughout the pulled silicon wafer on the basis of the light transmission characteristic ($I_{OBS}$) of the pulled silicon wafer measured during the first step and the light transmission characteristic ($I_O$) of the floating zone silicon wafer measured during the second step.

2. The method of claim 1, further including:

(d) a fourth step of comparing the substitutional carbon concentration [$C_{SC}$] of the pulled silicon wafer measured during the third step with a reference value.

3. The method of claim 2, further including:

(e) a fifth step of removing the pulled silicon wafer if its substitutional carbon concentration [$C_{SC}$] is not within a range of values about the reference value and thereby determined to be defective.

4. The method of claim 1, wherein steps (a) and (b) each comprise the step of providing said parallel polarized light across a range of infrared light.

5. The method of claim 4, wherein said providing step comprises the steps of:

(i) emitting light from a globe lamp;

(ii) receiving said light from the globe lamp and producing interference light therefrom; and (iii) filtering said interference light to provide said parallel polarized light.

6. A silicon wafer production method in which a pulled silicon wafer cut from a pulled silicon single crystal is subject to a series of treatments, said production method comprising the steps of:

(a) a first step of measuring a light transmission characteristic ($I_{OBS}$) of the pulled silicon wafer by utilizing parallel polarized light incident at a Brewster angle into the pulled silicon wafer, wherein the Brewster angle is an angle defined between the parallel polarized light and a line which is perpendicular to a face of the pulled silicon wafer;

(b) a second step of measuring a light transmission characteristic ($I_O$) of a floating zone silicon wafer functioning as a reference silicon wafer both front and rear faces of which are mirror polished, by utilizing parallel polarized light incident at the Brewster angle into the floating zone silicon wafer; and (c) a third step of directly calculating a substitutional carbon concentration throughout the pulled silicon wafer on the basis of the light transmission characteristic ($I_{OBS}$) of the pulled silicon wafer measured during the first step and the light transmission characteristic ($I_O$) of the floating zone silicon wafer measured during the second step.

7. A silicon wafer production method as defined in claim 6, in which the series of treatments include mechanical cutting, mechanical polishing, chemically polishing, mirror polishing, detecting defective wafers, removing defective wafers, washing, and gettering.

8. The method of claim 6, wherein steps (a) and (b) each comprise the step of providing said parallel polarized light across a range of infrared light.

9. The method of claim 8, wherein said providing step comprises the steps of:
   (i) emitting light from a globe lamp;
   (ii) receiving said light from the globe lamp and producing interference light therefrom; and
   (iii) filtering said interference light to provide said parallel polarized light.

10. A silicon wafer production method comprising the steps of:
    (a) a first step of measuring a light transmission characteristic or transmitted light intensity ($I_{OBS}$) of a pulled silicon wafer both front and rear surfaces of which are chemically polished within a production line and then washed, by utilizing parallel polarized light incident at a Brewster angle (B) into the pulled silicon wafer, wherein the Brewster angle (B) is an angle defined between the parallel polarized light and a line which is perpendicular to a face of the chemically polished pulled silicon wafer;
    (b) a second step of measuring a light transmission characteristic or transmitted light intensity ($I_O$) of a floating zone silicon wafer functioning as a reference silicon wafer both front and rear faces of which are mirror polished, by utilizing parallel polarized light at the Brewster angle (B) into the reference silicon wafer or floating zone silicon wafer; and
    (c) a third step of directly calculating a substitutional carbon concentration throughout the chemically polished pulled silicon wafer on the basis of the light transmission characteristic or transmitted light intensity ($I_{OBS}$) of the chemically polished pulled silicon wafer measured during the first step and the light transmission characteristic or transmitted light intensity ($I_O$) of the mirror polished floating zone silicon wafer or reference silicon wafer measured during the second step.

11. The pulled silicon wafer measuring method of claim 10, further including:
    (d) a fourth step of comparing the substitutional carbon concentration [$C_{SC}$] of the pulled silicon wafer measured during the third step with a reference value.

12. The pulled silicon wafer measuring method of claim 11, further including:
    (e) a fifth step of removing a pulled silicon wafer if its substitutional carbon concentration [$C_{SC}$] is not within a range of values about the reference value and thereby determined to be defective.

13. The method of claim 10, wherein steps (a) and (b) each comprise the step of providing said parallel polarized light across a range of infrared light.

14. The method of claim 13, wherein said providing step comprises the steps of:
    (i) emitting light from a globe lamp;
    (ii) receiving said light from the globe lamp and producing interference light therefrom; and
    (iii) filtering said interference light to provide said parallel polarized light.

15. A silicon wafer production method comprising the steps of:
    (a) a first step of measuring a light transmission characteristic or transmitted light intensity ($I_{OBS}$) of a one-face polished pulled silicon wafer only a front face of which is mirror polished within a production line and then washed, by utilizing parallel polarized light incident at a Brewster angle (B) into the pulled silicon wafer, wherein the Brewster angle (B) is an angle defined between the parallel polarized light and a line which is perpendicular to a face of the one-face polished pulled silicon wafer;
    (b) a second step of measuring a light transmission characteristic or transmitted light intensity ($I_O$) of a floating zone silicon wafer functioning as a reference silicon wafer by utilizing parallel polarized light incident at the Brewster angle (B) into the reference silicon wafer or floating zone silicon wafer; and
    (c) a third step of directly calculating a substitutional carbon concentration throughout the one-face polished pulled silicon wafer on the basis of the light transmission characteristic or transmitted light intensity ($I_{OBS}$) of the one-face polished pulled silicon wafer measured during the first step and the light transmission characteristic or transmitted light intensity ($I_O$) of the mirror polished floating zone silicon wafer or reference silicon wafer measured during the second step.

16. The pulled silicon wafer measuring method of claim 15, further including:
    (d) a fourth step of comparing the substitutional carbon concentration [$C_{SC}$] of the pulled silicon wafer measured during the third step with a reference value.

17. The pulled silicon wafer measuring method of claim 16, further including:
    (e) a fifth step of removing a pulled silicon wafer if its substitutional carbon concentration [$C_{SC}$] is not within a range of values about the reference value and thereby determined to be defective.

18. The method of claim 15, wherein steps (a) and (b) each comprise the step of providing said parallel polarized light across a range of infrared light.

19. The method of claim 18, wherein said providing step comprises the steps of:
    (i) emitting light from a globe lamp;
    (ii) receiving said light from the globe lamp and producing interference light therefrom; and
    (iii) filtering said interference light to provide said parallel polarized light.

20. A method for measuring a substitutional carbon concentration, said method comprising the steps of:
    (1) providing a pulled silicon wafer, said pulled silicon wafer having a substitutional carbon concentration to be measured and having a front face and a rear face, said front face having one of a plurality of predetermined finishes and said rear face having one of said plurality of predetermined finishes,
    (2) providing a floating zone silicon wafer, said floating zone silicon wafer functioning as a reference silicon wafer and having both front and rear faces which are mirror polished;
    (3) measuring a first light transmission characteristic of said pulled silicon wafer by utilizing parallel polarized light incident at a Brewster angle into said pulled silicon wafer, wherein the Brewster angle is an angle defined between the parallel polarized light and a line which is perpendicular to a face of said pulled silicon wafer;

(4) measuring a second light transmission characteristic of said floating zone silicon wafer by utilizing parallel polarized light incident at the Brewster angle into said floating zone silicon wafer; and (5) calculating said substitutional carbon concentration throughout said pulled silicon wafer on the basis of said first light transmission characteristic and said second light transmission characteristic.

21. A method as recited in claim 2, wherein said plurality of predetermined finishes include a chemically polished finish and a mirror polished finish.

22. The method of claim 20, wherein steps (3) and (4) each comprise the step of providing said parallel polarized light across a range of infrared light.

23. The method of claim 22, wherein said providing step comprises the steps of:
(i) emitting light from a globe lamp;
(ii) receiving said light from the globe lamp and producing interference light therefrom; and
(iii) filtering said interference light to provide said parallel polarized light.

\* \* \* \* \*